(12) United States Patent
Thomas, Jr.

(10) Patent No.: US 8,414,549 B1
(45) Date of Patent: Apr. 9, 2013

(54) ANUS CLEANING APPARATUS

(76) Inventor: Christopher Y. Thomas, Jr., Prairie Village, KS (US)

( * ) Notice: Subject to any disclaimer, the term of this patent is extended or adjusted under 35 U.S.C. 154(b) by 11 days.

(21) Appl. No.: 13/016,220

(22) Filed: Jan. 28, 2011

(51) Int. Cl.
*A61M 31/00* (2006.01)

(52) U.S. Cl. ........ 604/275; 604/279; 604/212; 604/911; 604/36

(58) Field of Classification Search ............ 604/275, 604/277–279, 212, 257, 276, 911, 36, 37, 604/39
See application file for complete search history.

(56) References Cited

U.S. PATENT DOCUMENTS

| | | | | |
|---|---|---|---|---|
| 758,643 | A * | 5/1904 | Haigh | ............ 604/195 |
| 1,070,787 | A * | 8/1913 | Eggers | ............ 604/195 |
| 1,175,095 | A * | 3/1916 | Walker | ............ 604/212 |
| 1,716,539 | A | 6/1929 | De Spain | |
| 2,036,218 | A * | 4/1936 | Kammer | ............ 604/84 |
| 2,596,083 | A | 5/1949 | Wahlbeck | |
| 2,660,170 | A | 11/1953 | Kahl | |
| 2,664,893 | A * | 1/1954 | Kempel | ............ 604/212 |
| 3,499,444 | A | 3/1970 | Koutsandreas | |
| 3,557,788 | A * | 1/1971 | Swartz | ............ 604/195 |
| 4,391,280 | A | 7/1983 | Miller | |
| 5,219,337 | A | 6/1993 | Takata et al. | |
| 6,902,557 | B2 | 6/2005 | Mezzoli | |
| 8,147,445 | B2 * | 4/2012 | Cox | ............ 604/37 |
| 2004/0260252 | A1 * | 12/2004 | DiPiano et al. | ............ 604/275 |

* cited by examiner

*Primary Examiner* — Kevin C Sirmons
*Assistant Examiner* — Laura Schell

(57) ABSTRACT

A personal cleaning apparatus includes a housing that has a bottom wall and a peripheral wall. The peripheral wall has an upper edge defining an opening into the housing. A conduit has a first end and a second end and a perimeter wall extending between the first and second ends. The first and second ends are open. The upper edge of the peripheral wall is integrally attached to and coextensive with the conduit and the conduit is in fluid communication with an interior of the housing. An applicator includes a body portion and a top wall. The body portion has an open distal end with respect to the top wall that is positioned in the conduit. The top wall has a plurality of apertures extending therethrough. The housing may be filled with fluid, the applicator inserted into a person's body and the housing squeezed to eject the fluid.

7 Claims, 3 Drawing Sheets

ANUS CLEANING APPARATUS

BACKGROUND OF THE INVENTION

Field of the Invention

The present invention relates to cleaning devices and more particularly pertains to a new cleaning device for insertion into an anus.

SUMMARY OF THE INVENTION

The present invention meets the needs presented above by generally comprising a housing that has a bottom wall and a peripheral wall that is attached to and extends upwardly from the bottom wall. The peripheral wall has an upper edge defining an opening into the housing. The housing is comprised of a resiliently flexible material. A conduit has a first end and a second end and a perimeter wall extending between the first and second ends. The first and second ends are open. The upper edge of the peripheral wall is integrally attached to and coextensive with the conduit and the conduit is in fluid communication with an interior of the housing. An applicator includes a body portion and a top wall attached to the body portion. The body portion has a cylindrical shape having an open distal end with respect to the top wall. The body portion is positionable in and frictionally coupled to the conduit. The top wall has a convexly arcuate shape. The top wall has a plurality of apertures extending therethrough. The housing may be filled with fluid, the applicator inserted into a person's body and the housing squeezed to eject the fluid.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
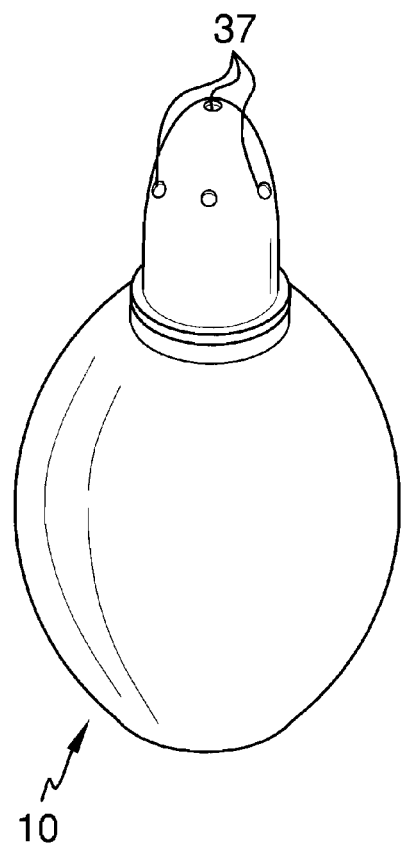
FIG. 1 is a perspective view of a personal cleaning apparatus according to the present invention.
Figure 2:
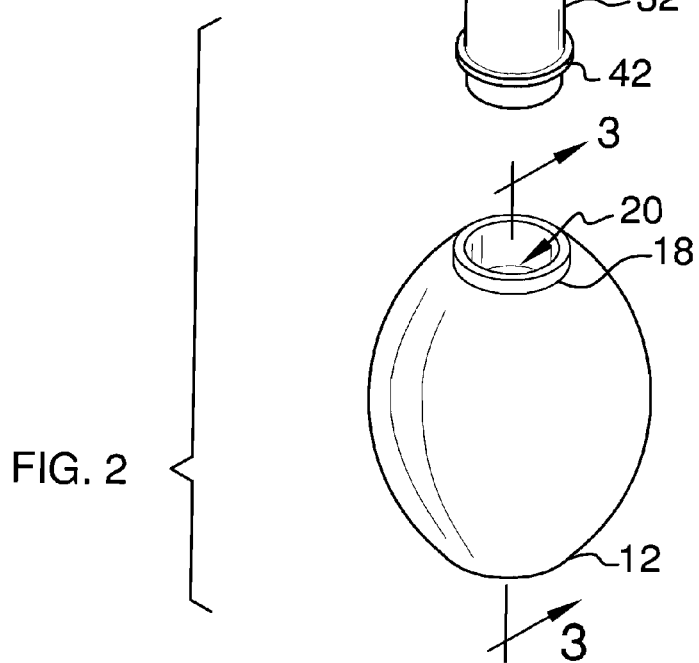
FIG. 2 is a perspective view expanded of the present invention.
Figure 3:
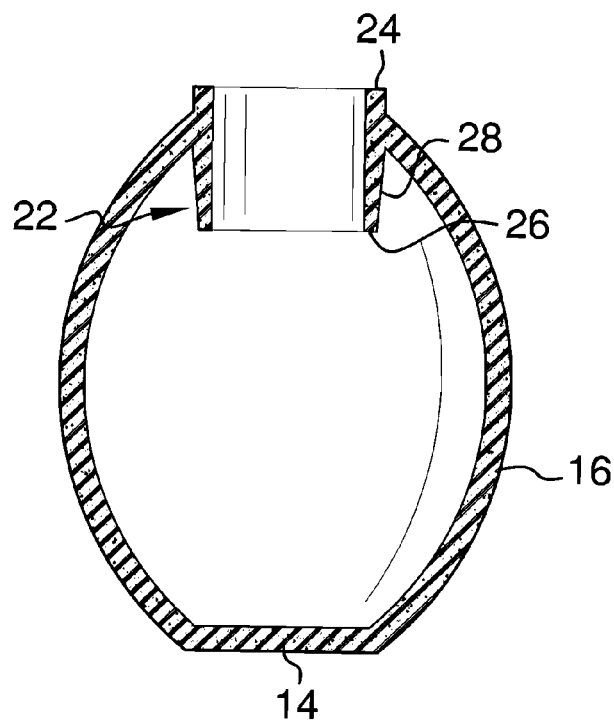
FIG. 3 is a cross-sectional view taken along line 3-3 of FIG. 2 of the present invention.
Figure 4:
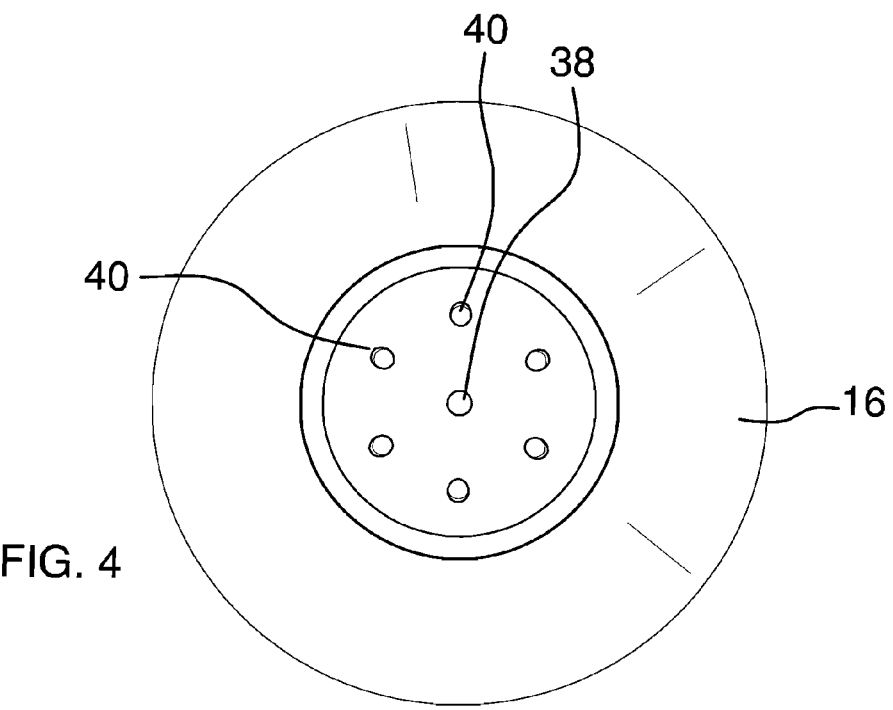
FIG. 4 is a top view of the present invention.
Figure 5:
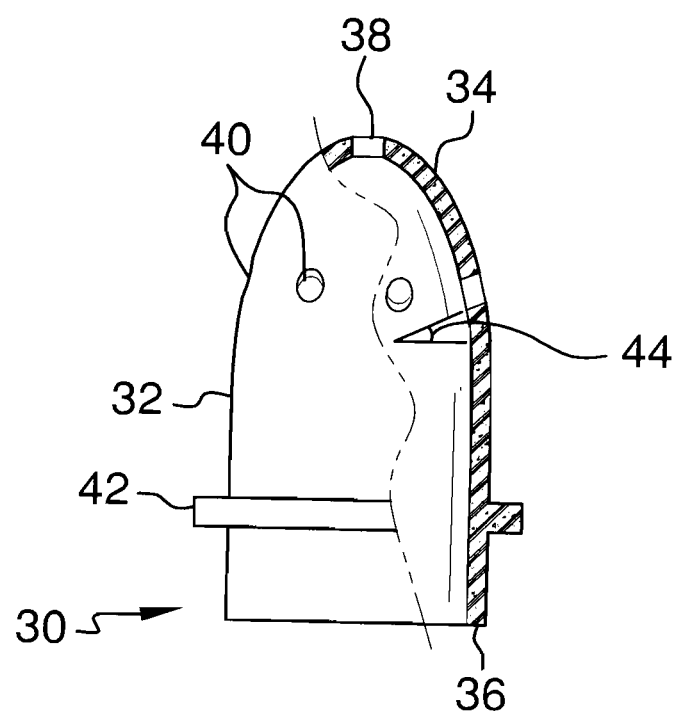
FIG. 5 is a broken side view of the applicator of the present invention.

With reference now to the drawings, and in particular to FIGS. 1 through 5 thereof, a new personal cleaning device embodying the principles and concepts of the present invention and generally designated by the reference numeral 10 will be described.

As best illustrated in FIGS. 1 through 5, the personal cleaning apparatus 10 generally comprises a housing 12 that has a bottom wall 14 and a peripheral wall 16 that is attached to and extends upwardly from the bottom wall 14. The peripheral wall 16 has an upper edge 18 defining an opening 20 into the housing 12. The housing 12 is comprised of a resiliently flexible material. The peripheral wall 16 has a convexly arcuate shape approximating a prolate spheroid and the bottom wall 14 is planar.

As best illustrated in FIGS. 1 through 5, the anus cleaning apparatus 10 generally comprises a housing 12 that has a bottom wall 14 and a peripheral wall 16 that is attached to and extends upwardly from the bottom wall 14. The peripheral wall 16 has an upper edge 18 defining an opening 20 into the housing 12. The housing 12 is comprised of a resiliently flexible material. The peripheral wall 16 has a convexly arcuate shape approximating a prolate spheroid and the bottom wall 14 is planar.

A conduit 22 has a first end 24 and a second end 26 and a perimeter wall 28 extends between the first 24 and second 26 ends. The first 24 and second 26 ends are open. The upper edge 18 of the peripheral wall 16 is integrally attached to and coextensive with the conduit 22 and the conduit 22 is in fluid communication with an interior of the housing 12. The first end 24 is positioned outside of the housing 12 and the second end 26 is positioned within the housing 12. The conduit 22 has a height from the first end 24 to the second end 26 less than 1½ inches.

An applicator 30 includes a body portion 32 and a top wall 34 attached to the body portion 32. The body portion 32 has a cylindrical shape that has an open distal end 36 with respect to the top wall 34. The body portion 32 is positionable in and frictionally coupled to the conduit 22. The top wall 34 has a convexly arcuate shape. The top wall 34 has a plurality of apertures 37 extending therethrough. The plurality of apertures 36 includes a primary opening 38 that is centrally located in the top wall 34. The plurality of apertures 37 includes a plurality, and at least three, of secondary openings 40 that are angled approximately between 50 degrees and 70 degrees away from the primary opening 38. This forms an angle 44 equal to about 30 degrees with respect to a plane of the distal end 36. The applicator 30 has a height from the distal end 36 to an apex of the top wall 34 less than 2 inches.

A perimeter lip 42 is attached to and extends around the body portion 32. The lip 42 is spaced from the distal end 36. The lip 42 is abutted against the first end 24 of the conduit 22 when the body portion 32 is extended into the conduit 22. The lip 42 extends away from the body portion 32 a distance approximately equal to a width of the perimeter wall 28 at the first end 24.

In use, the housing 12 may be filled with fluid and the applicator 30 inserted into a person's body. The housing 12 is squeezed to inject the fluid into the body. The positioning of the apertures 37 ensures that they will be able to eject the fluid. The fluid may be used for cleaning purposes. The apparatus 10 is particularly useful for persons wishing to prevent the soiling of their underpants.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A personal hygiene apparatus comprising:
a housing having a bottom wall and a peripheral wall being attached to and extending upwardly from said bottom wall, said peripheral wall having an upper edge defining an opening into said housing, said housing being comprised of a resiliently flexible material;
a conduit having a first end and a second end and a perimeter wall extending between said first and second ends, said first and second ends being open, said upper edge of said peripheral wall being integrally attached to and coextensive with said conduit and said conduit being in fluid communication with an interior of said housing;
an applicator including a body portion and a top wall being attached to said body portion, said body portion having a cylindrical shape having an open distal end with respect to said top wall, said body portion being positionable in and frictionally coupled to said conduit, said top wall having a convexly arcuate shape, said top wall having a plurality of apertures extending therethrough, said applicator having a height from said distal end to an apex of said top wall being less than 2 inches;
said apertures including angled openings extending outwardly through said body portion and being angled upwardly toward said top wall, said plurality of apertures includes a primary opening being centrally located in said top wall; and
wherein said first end of said conduit is positioned outside of said housing, said second end being positioned within said housing, further including a perimeter lip being attached to and extending around said body portion, said lip being spaced from said distal end, said lip being abutted against said first end of said conduit when said body portion is extended into said conduit, an outer surface of said applicator being smooth from said top wall to said lip except for said apertures and being free of any protrusions.

2. The apparatus according to claim 1, wherein said peripheral wall has a convexly arcuate shape approximating a prolate spheroid, said bottom wall being planar.

3. The apparatus according to claim 1, wherein said angled openings define secondary openings.

4. The apparatus according to claim 3, wherein said secondary openings are angled approximately between 50 degrees and 70 degrees away from said primary opening.

5. The apparatus according to claim 1, wherein said lip extends away from said body portion a distance approximately equal to a width of said perimeter wall at said first end.

6. A personal hygiene apparatus comprising
a housing having a bottom wall and a peripheral wall being attached to and extending upwardly from said bottom wall, said peripheral wall having an upper edge defining an opening into said housing, said housing being comprised of a resiliently flexible material, said peripheral wall having a convexly arcuate shape approximating a prolate spheroid, said bottom wall being planar;
a conduit having a first end and a second end and a perimeter wall extending between said first and second ends, said first and second ends being open, said upper edge of said peripheral wall being integrally attached to and coextensive with said conduit and said conduit being in fluid communication with an interior of said housing, said first end being positioned outside of said housing, said second end being positioned within said housing;
an applicator including a body portion and a top wall being attached to said body portion, said body portion having a cylindrical shape having an open distal end with respect to said top wall, said body portion being positionable in and frictionally coupled to said conduit, said top wall having a convexly arcuate shape, said top wall having a plurality of apertures extending therethrough, said plurality of apertures including a primary opening being centrally located in said top wall, said plurality of apertures including a plurality of secondary openings being angled approximately between 50 degrees and 70 degrees away from said primary opening, said applicator having a height from said distal end to an apex of said top wall being less than 2 inches; and
a perimeter lip being attached to and extending around said body portion, said lip being spaced from said distal end, said lip being abutted against said first end of said conduit when said body portion is extended into said conduit, said lip extending away from said body portion a distance approximately equal to a width of said perimeter wall at said first end, an outer surface of said applicator being smooth from said top wall to said lip except for said apertures and being free of any protrusions.

7. The apparatus according to claim 6, wherein said plurality of said apertures consists only of said primary opening and said secondary openings such that none of said apertures are angled more than 70 degrees away from said primary opening.

* * * * *